US007833517B2

(12) United States Patent
Fack et al.

(10) Patent No.: US 7,833,517 B2
(45) Date of Patent: Nov. 16, 2010

(54) TRANSPARENT OIL-IN-WATER EMULSION COSMETIC TREATMENT COMPOSITION

(75) Inventors: Geraldine Fack, Levallois-Perret (FR); Jonathan Gawtrey, Boulogne-Billancout (FR); Luc Nicolas-Morgantini, Rully (FR); Serge Restle, Saint-Prix (FR)

(73) Assignee: L'Oreal, Paris (FR)

( * ) Notice: Subject to any disclaimer, the term of this patent is extended or adjusted under 35 U.S.C. 154(b) by 1282 days.

(21) Appl. No.: 10/250,369

(22) PCT Filed: Jan. 2, 2002

(86) PCT No.: PCT/FR02/00004

§ 371 (c)(1),
(2), (4) Date: Dec. 18, 2003

(87) PCT Pub. No.: WO02/053113

PCT Pub. Date: Jul. 11, 2002

(65) Prior Publication Data

US 2004/0091437 A1    May 13, 2004

(30) Foreign Application Priority Data

Jan. 2, 2001  (FR) ................................. 01/00015
Jul. 2, 2001  (FR) ................................. 01/08759

(51) Int. Cl.
*A61Q 5/12*   (2006.01)
*A61Q 5/00*   (2006.01)

(52) U.S. Cl. ............... 424/70.19; 424/70.27; 424/70.28
(58) Field of Classification Search ....................... None
See application file for complete search history.

(56) References Cited

U.S. PATENT DOCUMENTS

| 5,344,643 | A  | * | 9/1994 | Thiel et al. ............... 424/70.11 |
| 6,602,494 | B1 | * | 8/2003 | Jahedshoar et al. ........ 424/70.1 |
| 7,476,393 | B2 | * | 1/2009 | Dubief et al. ............... 424/401 |

FOREIGN PATENT DOCUMENTS

| EP | 0 331 833    | 9/1989  |
| EP | 0 576 748    | 1/1994  |
| EP | 0 717 978    | 6/1996  |
| EP | 0 782 846    | 7/1997  |
| WO | WO 99/66883  | 12/1999 |
| WO | WO 01/28506  | 4/2001  |

* cited by examiner

*Primary Examiner*—Jyothsna A Venkat
(74) *Attorney, Agent, or Firm*—Steptoe & Johnson LLP

(57) ABSTRACT

A transparent composition for cosmetic treatment of keratinous materials comprising, in a cosmetically acceptable medium, at least a compound selected among polyols and mineral electrolytes, at least a volatile silicone, at least a siliconized surfactant, and at least a cationic surfactant in a concentration strictly higher than 0.5 wt. % relative to the composition total weight. The proportions of the polyols and mineral electrolytes are such that the (polyol and/or electrolyte)/oil ratio is not less than 2, the oil comprising at least the volatile silicone. A method for cosmetic treatment of keratinous materials using the transparent composition is also disclosed.

21 Claims, No Drawings

TRANSPARENT OIL-IN-WATER EMULSION COSMETIC TREATMENT COMPOSITION

The present invention relates to a transparent water-in-oil emulsion type composition for cosmetic treatment of keratinous materials and a method for cosmetic treatment of keratinous materials using the composition.

Water-in-oil type emulsions are well known in the field of cosmetic compositions.

However, these water-in-oil type emulsions are sensitive to temperature changes and thus present problems of stability depending on the surrounding temperature. In fact, a discrete separation of the aqueous and oil phase has been observed at low temperatures and at elevated temperatures.

Water-in-oil type emulsions having thermal stability have been previously described in EP 0 331 833 by Shiseido. They comprise a cationic surfactant, an oil phase and at least one polyoxyethylene organopolysiloxane. These emulsions are thermally stable in virtue of, among other things, the addition of a clay in a 0.2 to 5.0% by weight quantity relative to the total weight of the emulsion.

The inventors have unexpectedly found that by using certain proportions of a compound chosen from the group comprising the polyols and mineral electrolytes in the water-in-oil type emulsions, and especially in hair conditioners, that contain a volatile silicone oil, a silicone surfactant and a cationic surfactant, the latter being contained in a quantity greater than 0.5% by weight relative to the composition, the thermal stability of the compositions is improved.

Furthermore, the use of this type of compound in these compositions makes it possible to obtain, as another interesting result, transparent water-in-oil type emulsions. This use thus makes it possible also to improve the appearance of the cosmetic products and to make the product more attractive to the consumer.

The object, therefore, of the present invention is a transparent, water-in-oil type emulsion composition for treating keratinous materials, comprising in a cosmetically acceptable medium, at least one compound chosen from the group comprising the polyols and the mineral electrolytes, at least one volatile silicone, at least one silicone surfactant and at least one cationic surfactant at a concentration strictly greater than 0.5% by weight relative to the total weight of the composition.

Another object of the invention is a cosmetic treatment method for keratinous materials implementing a transparent composition according to the invention as described hereinafter.

A still further object of the invention is the use of the transparent composition according to the invention as a hair conditioner.

Other objects, characteristics, aspects and advantages of the invention will become more apparent when reading the description and the various examples that follow.

According to the invention, the transparent water-in-oil emulsion type cosmetic treatment composition for keratinous materials comprises in a cosmetically acceptable medium, at least one compound chosen from the group comprising the polyols and the mineral electrolytes, at least on volatile silicone, at least one silicone surfactant and at least one cationic surfactant at a concentration strictly greater than 0.5% by weight relative to the total weight of the composition.

"Transparent composition" is defined as a composition having a turbidity of less than or equal to 300 NTU, NTU being the nephelometric turbidity measurement unit.

Turbidity can be measured, for example, using a Model 2100P turbidimeter sold by the HACH Company, the tubes used for the measurement being referenced as N° AR397A, catalog 24347-06.

Calibration is done using formazin and measurements are carried out at room temperature (20 to 25° C.). The compositions of the invention preferably have a turbidity ranging from 0.05 to 100 NTU.

The transparent composition according to the invention has, in particular, a minimum penetration resistance of 0.075 N, as measured by penetrometry, and preferably less than 50 N, more preferably still less than 5 N.

The penetrometry measurements were done using a TA-TX2 (Rheo) texture analyzer. They correspond to measurements of compression force under following conditions:
(1) displacement of a disk (ebonite cylinder with a 13 mm diameter) at a rate of 1 mm/s and detection of the compression resistance;
(2) penetration into the product at the same rate as the aforementioned to a depth of 10 mm;
(3) maintenance of compression in the product at that depth for 300 s, and
(4) removal of the probe and detection of the breaking force at the rate of 1 mm/s.

"Polyol" is defined as any $C_3$-$C_{50}$, preferably $C_3$-$C_{20}$, hydrocarbon compound comprising at least two hydroxyl groups, and preferably from 2 to 10 hydroxyl groups.

The polyols particularly preferred in the present invention are chosen from the group comprising the sugars such as sorbitol and glycerin, and the $C_3$-$C_{20}$ alkylene polyols such as propylene glycol, and the $C_3$-$C_{20}$ polyethylene glycols such as PEG 300 and PEG 400.

The quantity of polyols is preferably in the range of 15 to 55% by weight, and especially in the range of 20 to 50%, relative to the total weight of the composition.

The mineral electrolytes well known in the related art can be used. The electrolytes used preferentially in the present invention are in particular the water-soluble monovalent or divalent metal salts of a mineral acid.

More particularly, electrolytes whose solubility in water is between 0.1% by weight and 300% by weight, and better still between 5 and 50% by weight, relative to the total weight of the aqueous solution, are preferably used.

By way of example, sodium chloride, potassium chloride, calcium chloride, magnesium chloride, magnesium sulfate, and sodium salts of phosphoric acid can be especially mentioned. Preferably, the monovalent metal salts and sodium chloride are particularly preferred.

The quantity of mineral electrolytes is preferably in the range from 0.1 to 20% by weight, and especially in the range from 0.5 to 15%, relative to the total weight of the composition.

The proportions of polyol(s) and/or electrolyte(s) are such that the ratio of (polyol(s) and/or electrolyte(s))/oils is greater than or equal to 2, preferably between 2 and 10, and more preferably between 2 and 5.

"Oil" is defined in the present invention as any fatty compound that is immiscible in water and which is liquid at room temperature.

According to the present invention, the oils comprise at least the volatile silicone and can comprise in addition at least one of the compounds chosen from the group comprising vegetable oils, animal oils, mineral oils, synthetic oils, fatty acid esters, and their mixtures.

Sweet almond oil, avocado oil, castor oil, olive oil, jojoba oil, sunflower oil, wheat germ oil, sesame oil, peanut oil, grapeseed oil, soya oil, rapeseed oil, safflower oil, coprah oil, corn oil, nut oil, karite butter, palm oil, apricot seed oil, and calophyllum oil can be mentioned in particular.

Perhydrosqualene can be mentioned in particular as animal oil.

Paraffin oil and vaseline oil can be mentioned in particular as mineral oils.

By way of examples of synthetic oils, squalane, the poly ((α-olefins) such as isododecane or isohexadecane, the transesterified vegetable oils, the fluorinated oils, and their mixtures can be mentioned.

As fatty acid esters, for example, the compounds having the formula $R_aCOOR_b$ wherein $R_a$ represents the residue of a higher fatty acid comprising 6 to 29 carbon atoms, and $R_b$ represents a hydrocarbon chain comprising 3 to 30 carbon atoms, such as purcellin oil (stearyl octanoate), isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate can be mentioned.

The oils are contained preferably in the composition according to the invention in a quantity of less than or equal to 20% by weight, more preferably between 5 and 20% by weight, relative to the total weight of the composition.

The volatile silicones that can be used in the invention are the linear or cyclic silicones having a viscosity at room temperature and under atmospheric pressure of less than 8 mm²/s (8 cSt).

Viscosity is measured preferably by capillary viscosimetry, for example, using a capillary viscosimeter, especially of the Ubbelohde type, at a temperature of 25° C. according to the ASTM D445-97 standard. The method commonly known as the falling ball viscosimeter can also be used.

The volatile silicones generally have a boiling point of between 60° C. and 260° C. and are more particularly chosen from the group comprising:
  (i) the cyclic volatile silicones comprising 3 to 7 silicon atoms and preferably 4 to 5 silicon atoms; for example octamethylcyclotetrasiloxane sold especially under the name "VOLATILE SILICONE 7207" by UNION CARBIDE or "SILBIONE® 70045 V 2" by RHODIA; decamethylcyclopentasiloxane sold under the name of "VOLATILE SILICONE 7158" by UNION CARBIDE, "SILBIONE® 70045 V 5" by RHODIA or under the name DC245 Fluid by DOW CORNING, as well as their mixtures.

The dimethylsiloxane/methylalkylsiloxane cyclocopolymers can also be mentioned such as "SILICONE VOLATILE FZ 3109" sold by UNION CARBIDE and having the chemical structure:

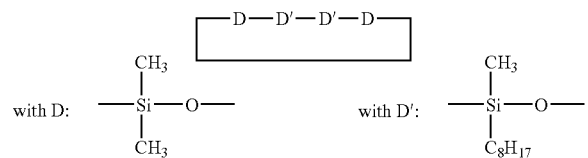

Mixtures of cyclic silicones with organic compounds derived from silicon such as the mixture of octamethylcyclotetrasiloxane and tetratrimethylsilyl pentaerythritol (50/50) and the mixture of octamethylcyclotetrasiloxane and oxy-1,1'-(hexa-2,2,2',2',3,3'-trimethylsilyloxy) bis-neopentane can also be mentioned;
  (ii) linear volatile silicones having 1 to 9 silicon atoms and having a viscosity of less than or equal to 5 mm²/s at 25° C.; for example, decamethyltetrasiloxane sold especially under the name "SH 200" by TORAY SILICONE. Silicones included in this class are also described in the article by TODD & BYERS published in Cosmetics and Toiletries, Vol. 91, January 1976, pp. 27-32, "Volatile silicone fluids for cosmetics."

The composition according to the invention comprises preferably the volatile silicones in a quantity of between 5 and 20% by weight, and more preferably between 8 and 15% by weight, relative to the total weight of the composition.

The silicone surfactants that can be used in the present invention are those well known to those skilled in the art. They can be water-soluble, spontaneously water-dispersible or non-water-soluble. Preferably, they are water-soluble or spontaneously water-dispersible.

The silicone surfactants are, for example, selected from the group comprising compounds of the general formulae (I), (II), (III), (IV) and (V):

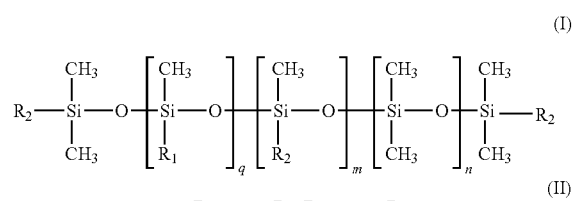

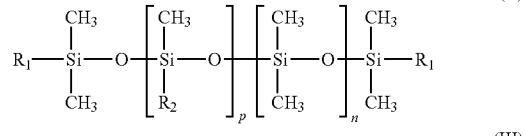

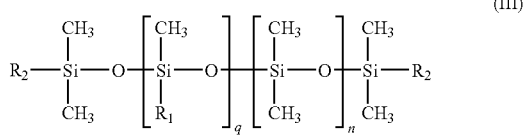

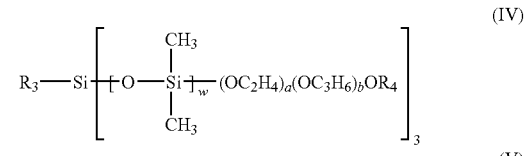

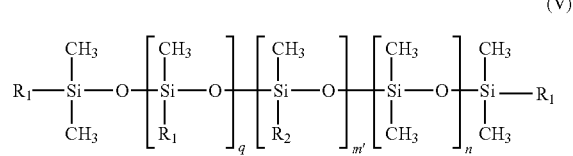

wherein:
  $R_1$, identical or different, represents a linear or branched $C_1$-$C_{30}$ alkyl or phenyl group;
  $R_2$, identical or different, represents —$C_cH_{2c}$—O—($C_2H_4O)_a$—($C_3H_6O)_b$—$R_5$ or —$C_6H_{2c}$O—($C_4H_8O)_a$—$R_5$;
  $R_3$ and $R_4$, identical or different, each designates a linear or branched $C_1C_{12}$ alkyl group and preferably a methyl group;
  $R_5$, identical or different, is chosen from a hydrogen atom, a linear or branched alkyl group comprising 1 to 12 carbon atoms, a linear or branched alkoxy group comprising from 1 to 6 carbon atoms, a linear or branched acyl group comprising 2 to 12 carbon atoms, a hydroxyl group, —$SO_3M$, —$OCOR_6$, $C_1$-$C_6$ aminoalkoxy, possibly substituted on the amine, $C_2$-$C_6$ aminoacyl, possibly substituted on the amine, —NHCH$_2$CH$_2$COOM, —N(CH$_2$CH$_2$COOM)$_2$, C$_1$-C$_{12}$ aminoalkyl, possibly substituted on the amine and on the alkyl chain, C$_1$-C$_{30}$ carboxyacyl, a phosphono group, possibly substituted by one or two substituted C$_1$-C$_{12}$ aminoalkyl, —CO(CH$_2$)$_d$(COOM), —OCOCHR$_7$(CH$_2$)$_d$COOM, —NHCO(CH$_2$)$_d$OH, and —NH$_3$Y groups;

M, identical or different, is a hydrogen atom, Na, K, Li, NH$_4$ or an organic amine;

R$_6$ is a linear or branched C$_1$-C$_{30}$ alkyl group;

R$_7$ is a hydrogen atom or an SO$_3$M group;

d varies from 1 to 10;

m varies from 0 to 20;

m' varies from 1 to 20;

n varies from 0 to 500;

p varies from 1 to 50;

q varies from 0 to 20;

a varies from 0 to 50;

b varies from 0 to 50;

a+b is greater than or equal to 1;

c varies from 0 to 4;

w varies from 1 to 100; and

Y represents a monovalent mineral or organic anion such as halide (chloride, bromide), sulfate, or carboxylate (acetate, lactate, citrate).

Preferably, silicone surfactants are used that are represented by the general formulae (I) or (II) as defined hereinbefore and, more particularly, those represented by the formulae (I) or (II), wherein at least one, and preferably all, of the following conditions are met:

c is equal to 2 or 3;

R$_1$ is a methyl group;

R$_2$ represents a hydrogen atom, a methyl group or an acetyl group and preferably a hydrogen atom;

a varies from 1 to 25, and more particularly from 2 to 25;

b varies from 0 to 25, preferably from 10 to 20;

n varies from 0 to 100; and p varies from 1 to 20.

The most particularly preferred silicone surfactants are, for example, those sold under the trade names FLUID DC 193 and DC 5225C by DOW CORNING, SILWET® L 77 by OSI and MAZIL® 756 by MAZER PPG.

The silicone surfactants are contained in the present invention in a quantity of between 0.01 and 10% by weight, more preferably between 0.1 and 5% by weight, and more preferably between 0.2 and 3% by weight, relative to the total weight of the composition for treating keratinous materials.

The composition according to the invention comprises one or more cationic surfactants well known per se such as the salts of primary, secondary or tertiary fatty amines, possibly polyoxylaklyened, the quaternary ammonium salts and their mixtures.

As quaternary ammonium salts, for example, the following can be especially mentioned:

(1) those having the following general formula (VI):

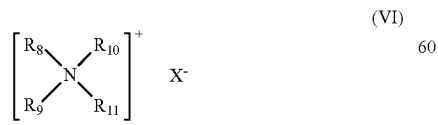

wherein the radicals R$_8$ to R$_{11}$, which can be identical or different, represent a linear or branched aliphatic radical comprising from 1 to 30 carbon atoms or an aromatic radical such as aryl or alkylaryl. The aliphatic radicals can comprise heteroatoms such as, in particular, oxygen, nitrogen, sulfur and halogens. The aliphatic radicals are, for example, chosen from the group comprising the alkyl, alkoxy, (C$_2$-C$_6$) polyoxyalkylene, alkylamide, (C$_{12}$-C$_{22}$) alkylamido (C$_2$-C$_6$) alkyl, (C$_{12}$-C$_{22}$) alkyl acetate, and hydroxyalkyl, comprising approximately from 1 to 30 carbon atoms; X is an anion chosen from the group of halides, phosphates, acetates, lactates, (C$_2$-C$_6$) alkyl sulfates, alkyl- or alkylaryl-sulfonates;

(2) the quaternary ammonium salts of imidazoline such as, for example, those having the following formula (VII):

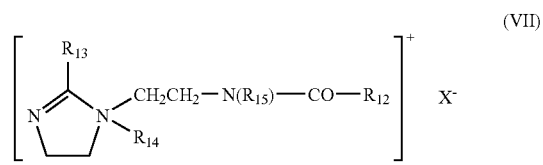

wherein R$_{12}$ represents an alkenyl or alkyl radical comprising from 8 to 30 carbon atoms, for example, derivatives of tallow fatty acids, R$_{13}$ represents a hydrogen atom, a C$_1$-C$_4$ alkyl radical or an alkenyl or an alkyl radical comprising 8 to 30 carbon atoms, R$_{14}$ represents a C$_1$-C$_4$ alkyl radical, R$_{15}$ represents a hydrogen atom, a C$_1$-C$_4$ alkyl radical, X$^-$ is an anion chosen from the group of halides, phosphates, acetates, lactates, alkyl sulfates, alkyl- or alkylarylsulfonates. Preferably, R$_{12}$ and R$_{13}$ are a mixture of alkenyl or alkyl radicals comprising from 12 to 21 carbon atoms, for example, derived from tallow fatty acids; R$_{14}$ is a methyl radical; R$_{15}$ is a hydrogen atom. This type of product is, for example, sold under the name REWOQUAT® W 75 by REWO;

(3) quaternary diammonium salts having the formula (VIII):

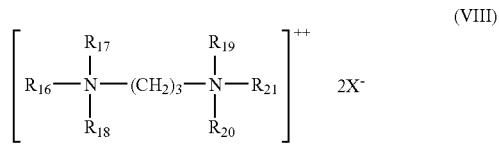

wherein R$_{16}$ is an aliphatic radical comprising approximately from 16 to 30 carbon atoms; R$_{17}$, R$_{18}$, R$_{19}$, R$_{20}$, and R$_{21}$, identical or different, are chosen from the group comprising hydrogen or an alkyl radical comprising from 1 to 4 carbon atoms and X is an anion chosen from the group comprising halides, acetates, phosphates, nitrates and methyl sulfates. These types of quaternary diammonium comprise in particular propane-tallow diammonium dichloride; and (4) the quaternary ammonium salts containing at least one ester function such as those of the following formula (IX):

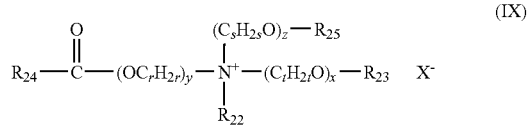

wherein
R$_{22}$ is chosen from the group comprising C$_1$-C$_6$ alkyl radicals and C$_1$-C$_6$ hydroxyalkyl or dihydroxyalkyl radicals;
R$_{23}$ is chosen from the group comprising:
(a) the

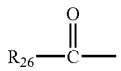

radical;
(b) the linear or branched, saturated or unsaturated; C$_1$-C$_{22}$ hydrocarbon R$_{27}$ radicals; and
(c) the hydrogen atom.
(a) the

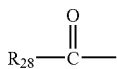

radical;
(b) the linear or branched, saturated or unsaturated C$_1$-C$_6$ hydrocarbon R$_{29}$ radicals; and
(c) the hydrogen atom.
R$_{25}$ is chosen from the group comprising:
the

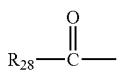

radical
the linear or branched, saturated or unsaturated C$_1$-C$_6$ hydrocarbon R$_{29}$ radicals;
the hydrogen atom;
R$_{24}$, R$_{26}$ and R$_{28}$, identical or different, are chosen from the group comprising the linear or branched, saturated or unsaturated C$_7$-C$_{21}$ hydrocarbon radicals;
r, s and t, identical or different, are integers with a value of 2 to 6;
y is an integer with a value of 1 to 10;
x and z, identical or different, are integers with values of from 0 to 10;
X$^-$ is a simple or complex, organic or inorganic anion;
providing that the sum x+y+z is 1 to 15, that when x is equal to 0 then R$_{23}$ is R$_{27}$ and when z is equal to 0 then R$_{25}$ is R$_{29}$.

The alkyl radicals R$_{22}$ can be linear or branched and more particularly linear.

Preferably, R$_{22}$ is a methyl, ethyl, hydroxyethyl, or dihydroxypropyl radical and, more particularly, a methyl or ethyl radical.

Advantageously, the sum x+y+z has a value of 1 to 10.

When R$_{23}$ is a hydrocarbon radical R$_{27}$, it can be long and have 12 to 22 carbon atoms or short and have 1 to 3 carbon atoms.

When R$_{25}$ is a hydrocarbon radical R$_{29}$, it has preferably 1 to 3 carbon atoms.

Advantageously, R$_{24}$, R$_{26}$ and R$_{28}$, identical or different, are chosen from the group comprising linear or branched, saturated or unsaturated C$_{11}$-C$_{21}$ hydrocarbon radicals and more particularly linear or branched, saturated or unsaturated C$_{11}$-C$_{21}$ alkyl and alkenyl radicals.

Preferably, x and z, identical or different, have a value of 0 or 1.

Advantageously, y is equal to 1.

Preferably, r, s and t, identical or different, have a value of 2 or 3 and, more particularly still, are equal to 2.

The anion is preferably a halide (chloride, bromide or iodide) or an alkyl sulfate, more particularly methyl sulfate. However, methane sulfonate, phosphate, nitrate, tosylate, an anion derived from an organic acid such as acetate or lactate or any other anion compatible with ammonium with an ester group.

The anion X$^-$ is more particularly chloride or methyl sulfate.

Ammonium salts having the following formula (IX) are more particularly used in the composition according to the invention, wherein:
R$_{22}$ is a methyl or ethyl radical
x and y are equal to 1;
z is equal to 0 or 1;
r, s and t are equal to 2;
R$_{23}$ is chosen from the group comprising:
R$_{22}$ is a methyl or ethyl radical;
x and y are equal to 1;
z is equal to 0 or 1;
r, s and t are equal to 2;
R$_{23}$ is chosen from the group comprising:
the

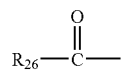

radical
the methyl, ethyl or C$_{14}$-C$_{22}$ hydrocarbon radicals;
the hydrogen atom;
R$_{25}$ is chosen from the group comprising:
the

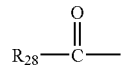

radical;
the hydrogen atom; and
R$_{24}$, R$_{26}$ and R$_{28}$, identical or different, are chosen from the group comprising the linear or branched, saturated or unsaturated C$_{13}$-C$_{17}$ hydrocarbon radicals and preferably from the group comprising the linear or branched, saturated or unsaturated C$_{13}$-C$_{17}$ alkyl and alkenyl radicals.

Advantageously, the hydrocarbon radicals are linear.

The compounds having the formula (IX) such as the salts (chloride or methyl sulfate, in particular) of diacyloxyethyl dimethyl ammonium, diacyloxyethyl hydroxyethyl methylammonium, monoacyloxyethyl dihydroxyethyl methyl ammonium, triacyloxyethyl methyl ammonium, monoacyloxyethyl hydroxyethyl dimethyl ammonium and their mixtures. The acyl radicals have preferably 14 to 18 carbon atoms and originate more particularly from a vegetable oil such as palm or sunflower oil. When the compound contains a plurality of acyl radicals, the latter can be identical or different.

These products are obtained, for example, by direct esterification of triethanolamine, triisopropanolamine, alkyldiethanolamine or alkyldiisopropanolamine, possibly oxyalkylenated on fatty acids or on mixtures of fatty acids of vegetable or animal origin, or by transesterification of their methyl esters. This esterification is followed by a quaternization using an alkylation agent such as an alkyl halide (preferably methyl or ethyl), a dialkyl sulfate (preferably methyl or ethyl), methyl methanesulfonate, methyl para-toluene-sulfonate, glycol or glycerol chlorhydrin.

These compounds are sold, for example, under the names DEHYQUART® by HENKEL, STEPANQUAT® by STEPAN, NOXAMIUM® by CECA, REWOQUAT® WE 18 by REQO-WITCO.

The composition according to the invention preferably contains a mixture of mono-, di- and triester salts of quaternary ammonium with a majority by weight of diester salts.

As a mixture of ammonium salts, for example, the mixture containing 15 to 30% by weight of acyloxyethyl dihydroxyethyl methyl ammonium methyl sulfate, 45 to 60% of diacyloxyethyl hydroxyethyl methyl ammonium methylsulfate and 15 to 30% of triacyloxyethyl methyl ammonium methylsulfate, the acyl radicals having 14 to 18 carbon atoms and originating from palm oil, possibly partially hydrogenated.

The ammonium salts containing at least one ester function disclosed in U.S. Pat. Nos. 4,874,554 and 4,237,180 can also be used.

Of the group of quaternary ammonium salts those that are represented by formula (VI) are particularly preferred, wherein:

$R_8$ represents a $C_{12-30}$ alkyl, preferably $C_{14-22}$ alkyl, $C_{12-30}$ alkenyl, ($C_{12-22}$) alkylamido($C_2$-$C_6$)alkyl, ($C_{12}$-$C_{22}$) alkyl acetate group or an aromatic group such as $C_6$-$C_{12}$ aryl or alkylaryl.

$R_9$ to $R_{11}$, which can be identical or different, represent a $C_{1-8}$ alkyl, $C_{1-8}$ alkenyl, $C_{1-8}$ alkoxy, $C_{1-8}$ hydroxyalkyl, ($C_2$-$C_6$) polyoxyalkylene or $C_{1-8}$ alkylamide group; and X is an anion chosen from the group comprising the halogenides, phosphates, acetates, lactates, ($C_2$-$C_6$) alkyl sulfates, alkyl- or alkylaryl-sulfonates.

By way of example of these particularly preferred compounds, on the one hand, the tetraalkyl ammonium salts, especially the tetraalkyl ammonium chlorides such as, for example, the dialkyl methyl ammonium or alkyl trimethyl ammonium chlorides can be mentioned, wherein the alkyl radical comprises approximately 12 to 30 carbon atoms, in particular the distearyl dimethyl ammonium, behenyl trimethyl ammonium, arachidyl trimethyl ammonium, stearyl trimethyl ammonium, cetyl trimethyl ammonium, benzyl dimethyl stearyl ammonium chlorides, or even, on the other hand, the ($C_8$-$C_{30}$) alkylamido($C_2$-$C_6$)alkyl trimethyl ammonium salts, especially the palmitylamidopropyl trimethyl ammonium chloride or stearamidopropyl dimethyl—(myristyl acetate) ammonium chloride sold under the name CERAPHYL® 70 by VAN DYK.

The cationic surfactants particularly preferred in the composition of the invention are chosen from the group comprising the quaternary ammonium salts and in particular from behenyl trimethyl ammonium chloride and palmitylamidopropyl trimethyl ammonium chloride.

The composition for cosmetic treatment of keratinous materials comprises preferably the cationic surfactant or surfactants and a quantity of between 0.5 and 10% by weight, better more preferably between 0.8 and 8% by weight, and most preferably between 1 and 5% by weight, relative to the total weight of the composition.

"Cosmetically acceptable medium" is defined as a medium that is compatible with all keratinous materials such as the skin, the hair, the nails, the eyelashes, the eyebrows, the lips and any other area of the body or the face, but also having a pleasant odor, appearance and texture.

The cosmetically acceptable medium comprises water or a mixture of oil and a cosmetically acceptable solvent chosen from the group comprising the $C_1$-$C_4$ lower alcohols, such as ethanol, isopropanol, tertiobutanol or n-butanol; the $C_5$-$C_{10}$ alkanes; the $C_{3-4}$ ketones such as acetone and methylethylketone; $C_1$-$C_4$ alkyl acetates such as methyl acetate, ethyl acetate and butyl acetate; dimethoxyethane, diethoxyethane, and their mixtures.

The pH of the compositions of the invention is between 3 and 12, preferably between 4 and 8.

Transparent compositions according to the invention can also contain additives such as cationic, anionic, non-ionic or amphoteric polymers; non-volatile silicones whether modified or not; associative or non-associative, anionic, amphoteric, zwitterionic, non-ionic or cationic, natural or synthetic, polymeric thickeners; sun filters; fragrances; coloring agents; organic or mineral particles; preservatives; and pH stabilizing agents.

Those skilled in the art will take care to choose any additives and the quantity thereof such that they do not harm the properties of the compositions of the present invention.

These additives are present in the composition according to the invention in a quantity ranging from 0 to 50% by weight relative to the total weight of the composition.

The compositions according to the invention can be in the form of fluid or thickened liquids, gels, creams, or single or multiple emulsions.

The compositions can be used, for example, as shampoos, hair conditioners, coloring products or bleaching or permanent wave products, hairdressing products, rinse treatments, deep treatment masks, shower gels, lotions or creams for scalp care, shaving products or depilation products.

The present invention also relates to a method for the cosmetic treatment of keratinous materials that consists of applying an effective quantity of a transparent composition such as that described above onto the keratinous materials, carrying out rinsing, if required, after an optional lapse of application time.

According to one preferred embodiment of the invention, the transparent composition can be used as a hair conditioner.

The following examples illustrate the present invention and should not be considered as limiting the invention in any fashion whatsoever.

EXAMPLES

Transparent hair conditioning compositions were prepared using the ingredients indicated in the following table. The indicated contents are expressed in % by weight relative to the total weight of the composition.

| | Ex. 1 | Ex. 2 | Ex. 3 |
|---|---|---|---|
| Cyclopentadimethylsiloxane [1] | 7 | 5.4 | 11.5 |
| Isopropyl myristate | — | 2.1 | — |
| Polydimethyl/methylsiloxane (18 moles of ethylene oxide/ 18 moles of propylene | 0.5 AS | 0.5 AS | 0.5 AS |

-continued

|  | Ex. 1 | Ex. 2 | Ex. 3 |
|---|---|---|---|
| oxide) [2] - DC 5225 (Dow Corning) |  |  |  |
| Palmitylamidopropyl trimethyl ammonium containing 60% AS in propylene glycol - Varisoft PATC (Goldschmidt) | 1.2 AS | 2.7 AS | 1.2 AS |
| Propylene glycol | 0.8 | 7.3 | 3.2 |
| NaCl | — | — | 9.7 |
| Sucrose | — | 29.5 | 19.35 |
| Glycerin | 40.8 | — | 1.2 |
| Water | 100 | 100 | 100 |

AS: Active substance
[1] DC 245 (Dow Corning)
[2] 10% in cyclopentadimethylsiloxane The compositions are applied to the hair and rinsed after a one-minute application time, with easy rinsing. Then the hair is dried.

The dried hair is soft and smooth to the touch and has no unpleasant residues.

These compositions are stable for 2 months at room temperature and at 45° C.

Turbidity of the compositions of Examples 1 and 2 are 75 NTU and 90 NTU, respectively.

The invention claimed is:

1. A transparent composition for the cosmetic treatment of keratinous materials in the form of a water-in-oil emulsion, comprising, in a cosmetically acceptable medium, at least one compound which is a polyol or mineral electrolyte, at least one volatile silicone in a quantity of between 5 and 20% by weight relative to the total weight of the composition, at least one silicone surfactant wherein the silicone surfactant is present in a quantity of between 0.01 and 10% by weight relative to the total weight of the composition, and at least one cationic surfactant wherein the cationic surfactant is present in a quantity of between 0.5 and 10% by weight relative to the total weight of the composition, wherein the ratio (polyol and/or electrolyte)/oil is greater than or equal to 2, wherein the at least one volatile silicone is a cyclic volatile silicone comprising 3 to 7 silicon atoms, wherein the cationic surfactant is a quaternary ammonium salt, the quaternary ammonium salt being a salt of formula (VI):

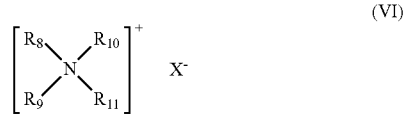

wherein:
X is an anion which is a halide, phosphate, acetate, lactate, ($C_2$-$C_6$) alkyl sulfate, or alkyl- or alkylarylsulfonate,
$R_8$ represents a ($C_{12}$-$C_{22}$) alkylamido($C_2$-$C_6$)alkyl or ($C_{12}$-$C_{22}$) alkyl acetate group, and
$R_9$ to $R_{11}$, which can be identical or different, represent a $C_{1-8}$ alkyl, $C_{1-8}$ alkenyl, $C_{1-8}$ alkoxy, $C_{1-8}$ hydroxyalkyl, ($C_2$-$C_6$) polyoxyalkylene or $C_{1-8}$ alkylamide group, wherein the silicone surfactant has the formula (II)

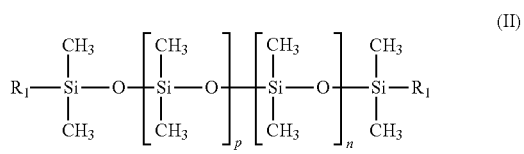

wherein:
a) $R_1$, identical or different, represents a linear or branched $C_1$-$C_{30}$ alkyl or phenyl group;
b) $R_2$, identical or different, represents —$C_cH_{2c}$—O—($C_2H_4O)_a$—($C_3H_6O)_b$—$R_5$ or —$C_6H_{2c}$O—($C_4H_8O)_a$—$R_5$;
c) $R_5$ identical or different, is a hydrogen atom, a linear or branched alkyl group comprising 1 to 12 carbon atoms, a linear or branched alkoxy group comprising 1 to 6 carbon atoms, a linear or branched acyl group comprising 2 to 12 carbon atoms, a hydroxyl group, —$SO_3M$, —$OCOR_6$, $C_1$-$C_6$-aminoalkoxy, optionally substituted on the amine, $C_2$-$C_6$ aminoacyl, optionally substituted on the amine, —$NHCH_2CH_2COOM$, —$N(CH_2CH_2COOM)_2$, $C_1$-$C_{12}$ aminoalkyl, optionally substituted on the amine and on the alkyl chain, $C_1$-$C_{30}$carboxyacyl, a phosphono group, optionally substituted by one or two substituted $C_1$-$C_{12}$ aminoalkyl, —$CO(CH_2)_d(COOM)$, —$OCOCHR_7(CH_2)_dCOOM$, —$NHCO(CH_2)_dOH$, or —$NH_3Y$ groups;
d) M, identical or different, is a hydrogen atom, Na, K, Li, $NH_4$ or an organic amine;
e) $R_6$ is a linear or branched $C_1$-$C_{30}$ alkyl group;
f) $R_7$ is a hydrogen atom or a $SO_3M$ group;
g) d is from 1 to 10;
h) n is from 0 to 500;
i) p is from 1 to 50;
j) a is from 0 to 50;
k) b is from 0 to 50;
l) a+b is greater than or equal to 1;
m) c varies from 0 to 4; and
n) Y represents a monovalent mineral or organic anion.

2. Transparent composition for the cosmetic treatment of keratinous materials according to claim 1, wherein the ratio of (polyol and/or electrolyte)/oil is between 2 and 10.

3. Transparent composition for the cosmetic treatment of keratinous materials according to claim 2, wherein the ratio of (polyol and/or electrolyte)/oil is between 2 and 5.

4. Transparent composition for the cosmetic treatment of keratinous materials according to claim 1, wherein the polyol is a sugar or $C_3$-$C_{20}$ alkylene polyol.

5. Transparent composition for the cosmetic treatment of keratinous materials according to claim 4, wherein the polyol is glycerin, sorbitol, propylene glycol or a $C_8$-$C_{20}$ polyethylene glycol.

6. Transparent composition for the cosmetic treatment of keratinous materials according to claim 1, wherein the polyol is present in a quantity ranging from 15 to 55% by weight relative to the total weight of the composition.

7. Transparent composition for the cosmetic treatment of keratinous materials according to claim 6, wherein the polyol is present in a quantity ranging from 20 to 50% by weight relative to the total weight of the composition.

8. Transparent composition for the cosmetic treatment of keratinous materials according to claim 1, wherein the mineral electrolyte is sodium chloride, potassium chloride, calcium chloride, magnesium chloride, magnesium sulfate, or a sodium salt of phosphoric acid.

9. Transparent composition for the cosmetic treatment of keratinous materials according to claim 1, wherein the mineral electrolyte is present in a quantity ranging from 0.1 to 20% by weight relative to the total weight of the composition.

10. Transparent composition for the cosmetic treatment of keratinous materials according to claim 9, wherein the mineral electrolyte is present in a quantity ranging from 0.5 to 15% by weight relative to the total weight of the composition.

11. Transparent composition for the cosmetic treatment of keratinous materials according to claim 1, wherein the volatile silicone is present in a quantity of between 8 and 15% by weight relative to the total weight of the composition.

12. Transparent composition for the cosmetic treatment of keratinous materials according to claim 1, wherein the silicone surfactant is represented by the formulae (II), wherein at least one, and optionally all, of the following conditions are satisfied:
  a) c is equal to 2 or 3;
  b) $R_1$ is a methyl group;
  c) $R_5$ represents a hydrogen atom, a methyl group or an acetyl group;
  d) a is an integer from 1 to 25;
  e) b is a integer from 0 to 25;
  f) n is an integer from 0 to 100; and
  g) p is an integer from 1 to 20.

13. Transparent composition for the cosmetic treatment of keratinous materials according to claim 1, wherein the silicone surfactant is present in a quantity of between 0.1 and 5% by weight relative to the total weight of the composition.

14. Transparent composition for the cosmetic treatment of keratinous materials according to claim 13, wherein the silicone surfactant is present in a quantity of between 0.2 and 3% by weight relative to the total weight of the composition.

15. Transparent composition for the cosmetic treatment of keratinous materials according to claim 1, wherein the cationic surfactant is present in a quantity of between 0.8 and 8% by weight relative to the total weight of the composition.

16. Transparent composition for the cosmetic treatment of keratinous materials according to claim 15, wherein the cationic surfactant is present in a quantity of between 1 and 5% by weight relative to the total weight of the composition.

17. Transparent composition for the cosmetic treatment of keratinous materials according to claim 1, wherein the cosmetically acceptable medium comprises water or a mixture of water and a cosmetically acceptable solvent.

18. Transparent composition for the cosmetic treatment of keratinous materials according to claim 17, wherein the cosmetically acceptable solvent is a $C_{1-4}$ lower alcohol, or $C_5$-$C_{10}$ alkane, $C_{3-4}$ ketone, $C_1$-$C_4$ alkyl acetate, dimethoxyethane, diethoxyethane, or mixtures thereof.

19. Transparent composition for the cosmetic treatment of keratinous materials according to claim 1, further comprising an additive which is a cationic, anionic, non-ionic or amphoteric polymer; non-volatile silicone, modified or unmodified; associative or non-associative, anionic, amphoteric, zwitterionic, non-ionic or cationic, natural or synthetic, polymeric thickener; sun filter; fragrance; coloring agent; organic or mineral particle; preservative; or pH stabilizing agent.

20. A method for the cosmetic treatment of keratinous materials, comprising applying a transparent composition for the cosmetic treatment of keratinous materials according to claim 1 to the keratinous materials.

21. Method for the cosmetic treatment of keratinous material according to claim 20, wherein the transparent composition is a hair conditioner.

* * * * *